US012702828B2

(12) United States Patent
Johari et al.

(10) Patent No.: US 12,702,828 B2
(45) Date of Patent: Aug. 11, 2026

(54) HANDHELD ELECTROSTIMULATION SKIN TREATMENT DEVICE

(71) Applicants: Pooja Johari, Miami, FL (US); Tejas Shah, Carlsbad, CA (US)

(72) Inventors: Pooja Johari, Miami, FL (US); Tejas Shah, Carlsbad, CA (US)

( * ) Notice: Subject to any disclaimer, the term of this patent is extended or adjusted under 35 U.S.C. 154(b) by 0 days.

(21) Appl. No.: 18/424,466

(22) Filed: Jan. 26, 2024

(65) Prior Publication Data

US 2024/0278007 A1 Aug. 22, 2024

Related U.S. Application Data

(63) Continuation of application No. 17/384,609, filed on Jul. 23, 2021, now Pat. No. 11,883,654.

(60) Provisional application No. 63/056,807, filed on Jul. 27, 2020.

(51) Int. Cl.
*A61N 1/32* (2006.01)
*A61N 1/04* (2006.01)

(52) U.S. Cl.
CPC ........... *A61N 1/328* (2013.01); *A61N 1/0452* (2013.01); *A61N 1/0484* (2013.01)

(58) Field of Classification Search
CPC ..... A61N 1/328; A61N 1/0452; A61N 1/0484
See application file for complete search history.

(56) References Cited

U.S. PATENT DOCUMENTS 11,883,654 B2 * 1/2024 Johari .................. A61N 1/0452
2003/0191508 A1 10/2003 Motoi
2007/0276449 A1 11/2007 Gunter et al.
2009/0287284 A1 11/2009 Soong et al.
2016/0361539 A1 12/2016 Nathanson et al.
2018/0099143 A1 4/2018 Kim et al.
2020/0179691 A1 6/2020 Chen
2021/0085969 A1 3/2021 Kim

* cited by examiner

*Primary Examiner* — William J Levicky
*Assistant Examiner* — Joshua Brendon Solomon
(74) *Attorney, Agent, or Firm* — Rutan & Tucker LLP; Hani Z. Sayed

(57) ABSTRACT

An electrostimulation treatment device is provided for performing handheld microcurrent muscle toning treatments in absence of the assistance of another person. The electrostimulation treatment device includes a handle section disposed between a treatment end and an accessories end. The treatment end includes one or more electrodes that are configured to supply an electric microcurrent to the skin and muscles of the user. The electrodes may be being pressed against the skin to manipulate the skin and muscles such that the muscles are forced into a desired form for re-education. The accessories end is adapted to receive one or more accessory connectors and a USB connector. The USB connector is configured to be coupled with an external computing device for operating the electrostimulation treatment device. The accessory connectors facilitate coupling the electrostimulation treatment device with external accessory devices, such as a lip mask, an eye mask, or a conductive glove.

19 Claims, 3 Drawing Sheets

136
140

148
144
148

152
156
164
164

168
156
168
160

172
184
180
176

HANDHELD ELECTROSTIMULATION SKIN TREATMENT DEVICE

PRIORITY

This application claims the benefit of and priority to U.S. patent application Ser. No. 17/384,609 filed on Jul. 23, 2021 and U.S. Provisional Application, entitled "Handheld Electrostimulation Skin Treatment Device," filed on Jul. 27, 2020 and having application Ser. No. 63/056,807, the entirety of said application being incorporated herein by reference.

FIELD

Embodiments of the present disclosure generally relate to electrostimulation devices. More specifically, embodiments of the disclosure relate to an apparatus for a handheld electrostimulation skin treatment device for skin toning and firming.

BACKGROUND

Electrostimulation is a well-known technology for non-invasive anti-aging treatments that enables users to age gracefully. Typically, electrostimulation devices tend to include microcurrent devices microcurrent devices that apply currents on the order of $10^{-6}$ amperes to the skin and underlying muscle of a user and millicurrent devices that apply larger currents, on the order of $10^{-3}$ amperes to the skin and underlying muscles of a user. Millicurrent devices generally apply an electric current to the skin and underlying muscle of a subject to cause involuntary rhythmic contractions of the muscles that improves muscle tone. Microcurrent devices are configured to apply much smaller currents, and thus microcurrent treatments do not cause muscle contractions and tend to be barely detectable by the subject.

Microcurrent treatments are known to increase the amount of adenosine triphosphate (ATP) within the cells of a muscle. For example, experimental demonstrations have shown that an application of a current on the order of 50 to 500 microamperes to the skin and underlying muscle of a subject can give rise to a 300-500% increase in ATP, as well as an increase in mitochondria and protein synthesis in the muscle, an increase in aminoisobutyric acid uptake, and an increase in protein synthesis and Gluconeogenesis (biosynthesis of new glucose). These dramatic increases in cellular ATP levels have been shown to help muscles retain a re-educated form for longer periods of time, and consequently such techniques are of use in muscle toning treatments.

As will be appreciated, for the benefits of muscle toning treatments to be appreciable it is necessary for the muscles to be manipulated, such as by way of extending or compressing the muscles, while the treatments are taking place. In a salon environment, microcurrent electrostimulation devices typically include a pair of probes that can be used by a technician during a treatment to manipulate the skin and muscle such that the muscles are forced into a desired form for re-education. In a home environment, however, subjects desiring microcurrent treatments generally find themselves without the assistance of another person. As such, there is a need for handheld microcurrent electrostimulation devices that are intended for personally performing muscle toning treatments in absence of the assistance of another person.

SUMMARY

An electrostimulation treatment device is provided for performing handheld microcurrent muscle toning treatments in absence of the assistance of another person. The electrostimulation treatment device includes a handle section disposed between a treatment end and an accessories end. The treatment end includes one or more electrodes that are configured to supply an electric microcurrent to the skin and muscles of the user. The electrodes may be being pressed against the skin to manipulate the skin and muscles such that the muscles are forced into a desired form for re-education. The accessories end is adapted to receive one or more accessory connectors and a USB connector. The USB connector is configured to be coupled with an external computing device for operating the electrostimulation treatment device. The accessory connectors facilitate coupling the electrostimulation treatment device with external accessory devices, such as a lip mask, an eye mask, or a conductive glove.

In an exemplary embodiment, an electrostimulation treatment device comprises: a handle section disposed between a first treatment end and a second treatment accessories end; one or more electrodes disposed on the treatment end; and a power switch disposed on the handle section.

In another exemplary embodiment, the handle section is adapted to be grasped in a hand of a practitioner. In another exemplary embodiment, the handle section includes a curvature along the length of the handle section that orients the treatment end away from the hand of the practitioner.

In another exemplary embodiment, the power switch is configured to enable the practitioner to turn the treatment device on and off, as desired. In another exemplary embodiment, a rechargeable battery and circuitry are enclosed within the handle section and configured to apply microcurrent electricity to the one or more electrodes when the power switch is turned on.

In another exemplary embodiment, the one or more electrodes are configured to supply electric current to the skin and muscles of the user. In another exemplary embodiment, the one or more electrodes are configured to be pressed against the skin so as to manipulate the skin and muscles such that the muscles are forced into a desired form for re-education. In another exemplary embodiment, the one or more electrodes comprise metallic spheres suitable for manipulating the skin and muscles of the user desiring a skin treatment.

In another exemplary embodiment, the accessories end is adapted to receive one or more accessory connectors and a USB connector. In another exemplary embodiment, the USB connector is configured to be coupled with an external computing device. In another exemplary embodiment, the USB connector is configured to be coupled to the second treatment accessory device. In another exemplary embodiment, the electrostimulation treatment device is configured to be operated by way of a software application running on the external computing device.

In another exemplary embodiment, the accessory connectors facilitate coupling the electrostimulation treatment device with external accessory devices. In another exemplary embodiment, the external accessory devices include any of a lip mask, an eye mask, forehead mask, jawline mask or a conductive glove. In another exemplary embodiment, the lip mask is configured to be coupled with the electrostimulation treatment device for the purpose of treating the skin comprising and/or surrounding the lips. In another exemplary embodiment, the eye mask is configured to be coupled with the electrostimulation treatment device for the purpose of treating the skin and muscles surrounding the eyes. In another exemplary embodiment, the conductive glove is configured to be coupled with the electrostimulation treatment device to facilitate manually manipulating the skin and muscles of the face while applying the electric microcurrent to the skin and muscles.

These and other features of the concepts provided herein may be better understood with reference to the drawings, description, and appended claims.

BRIEF DESCRIPTION OF THE DRAWINGS

The drawings refer to embodiments of the present disclosure in which.

Figure 1:
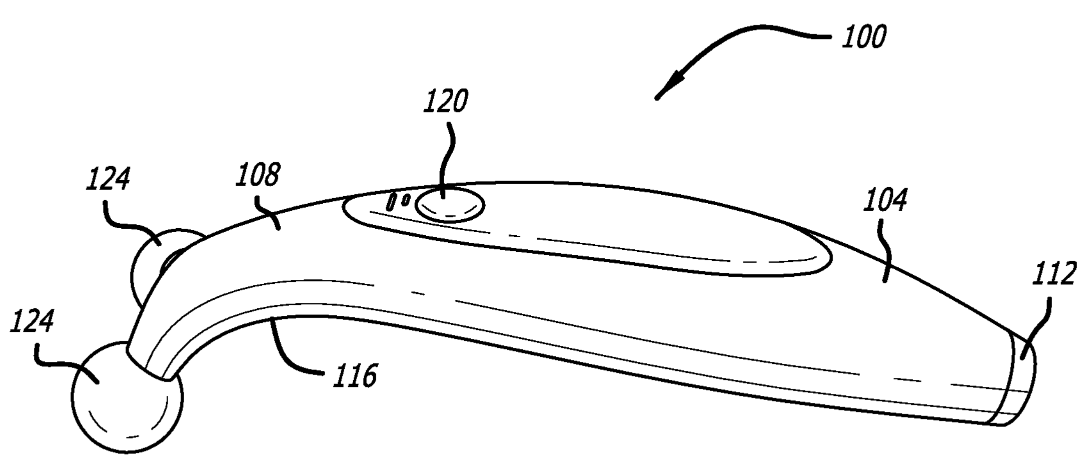
FIG. 1 illustrates a perspective view of an exemplary embodiment of a handheld electrostimulation skin treatment device, in accordance with the present disclosure.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first electrode," may be made. However, the specific numeric reference should not be interpreted as a literal sequential order but rather interpreted that the "first electrode" is different than a "second electrode." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

Electrostimulation is a well-known technology for non-invasive anti-aging treatments that enables users to age gracefully. Microcurrent treatments are known to increase the amount of adenosine triphosphate (ATP) within the cells of a muscle. Increases in cellular ATP levels have been shown to help muscles retain a re-educated form for longer periods of time, and as a consequence such techniques are of use in muscle toning treatments. In a salon environment, microcurrent electrostimulation devices typically include a pair of probes that can be used by a technician during a treatment to manipulate the skin and muscle such that the muscles are forced into a desired form for re-education. In a home environment, however, subjects desiring microcurrent treatments generally find themselves without the assistance of another person. Embodiments disclosed herein relate to an apparatus and methods for a handheld electrostimulation skin treatment device for skin toning and firming that are intended for personally performing muscle toning treatments in absence of the assistance of another person.

FIG. 1 illustrates a perspective view of an exemplary embodiment of a handheld electrostimulation skin treatment device (100), in accordance with the present disclosure. The treatment device 100 is a generally elongate member comprising a handle section 104 disposed between a treatment end 108 and an accessories end 112. The handle section 104 generally is adapted to be grasped in the hand of a practitioner using the device 100. The handle section 104 includes a curvature 116 along the length of the handle section 104 that orients the treatment end 108 away from the hand of the practitioner. Further, the handle section 104 includes a power switch 120 that enables the practitioner to turn the treatment device 100 on and off, as desired.

The treatment end 108 includes at least two electrodes 124 disposed on opposite sides of the treatment end 108. The electrodes 124 are configured to supply electric current to the skin and muscles of the user, particularly but not exclusively to facial skin and muscles. Further, the electrodes 124 generally are configured to be pressed against the skin so as to manipulate the skin and muscles such that the muscles are forced into a desired form for re-education. As shown in FIG. 1, the electrodes 124 comprise metallic spheres suitable for manipulating the skin and muscles of the user desiring a skin treatment. In some embodiments, a rechargeable battery and circuitry may be enclosed within the handle section 104 and configured to apply microcurrent electricity to the electrodes 124 when the power switch 120 is turned on.

Figure 2:
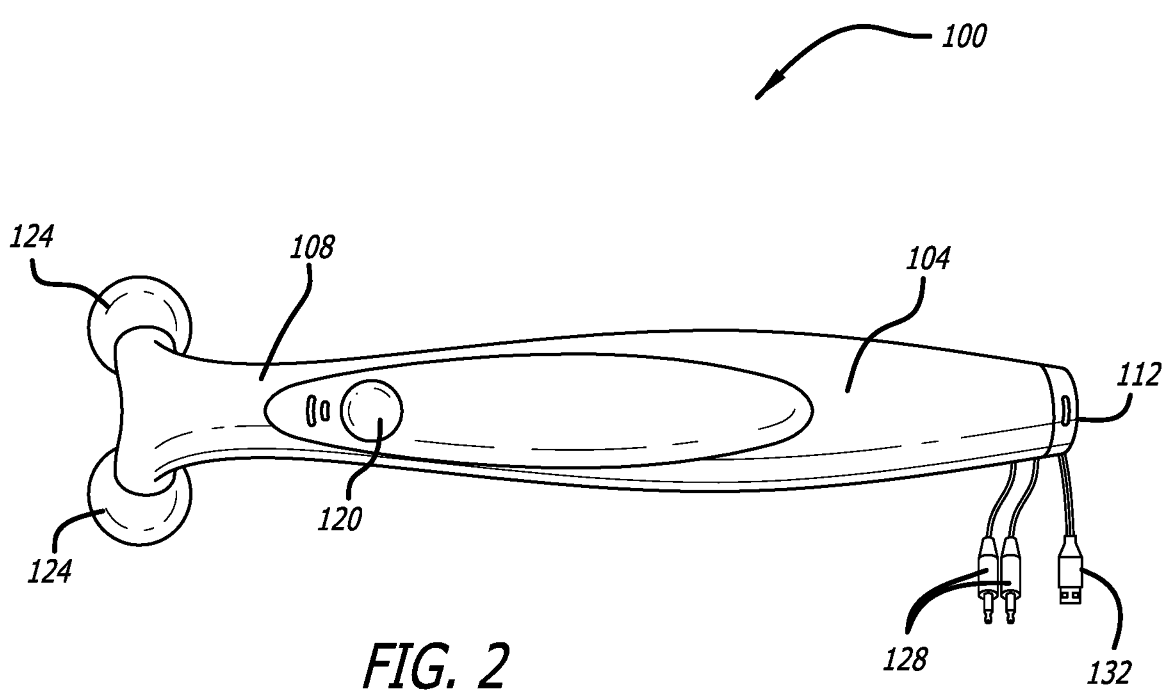
FIG. 2 illustrates a top view of an exemplary embodiment of a handheld electrostimulation skin treatment device, in accordance with the present disclosure.

As best shown in FIG. 2, the accessories end 112 is adapted to receive any of various accessory connectors 128 as well as a Universal System Bus (USB) connector 132 that may be coupled with an external computing device, such as a smartphone or tablet PC. As will be appreciated, the accessory connectors 128 facilitate coupling the treatment device 100 with external accessory devices that are configured to operate in conjunction with the device 100. Exemplary embodiments of external accessory devices suitable for use with the treatment device 100 are discussed hereinbelow.

Figure 3:
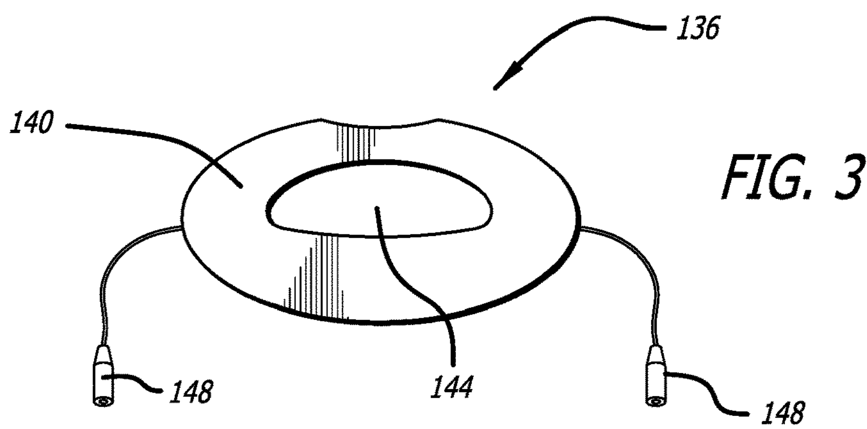
FIG. 3 illustrates a perspective view of an exemplary embodiment of a lip mask that may be coupled with the handheld electrostimulation skin treatment device of FIG. 1, according to the present disclosure.

FIG. 3 illustrates a perspective view of an exemplary embodiment of a lip mask 136 according to the present disclosure. The lip mask 136 is configured to be coupled with the treatment device 100 for the purpose of treating the skin comprising and/or surrounding the lips. As such, the lip mask 136 includes a conductive strip 140 that may be applied to the lip region of the face. The conductive strip 140 generally is configured to apply a suitable microcurrent to the lip region of the face. The lip mask 136 includes a mouth opening 144 that allow the user receiving treatment to breath and speak. Further, the lip mask 136 includes one or more electric connectors 148 that are configured to be plugged into the accessory connectors 128 of the treatment device 100 shown in FIG. 2. As will be appreciated, the electric connectors 148 and the accessory connectors 128 cooperate to pass electric microcurrent from the device 100 to the lip mask 136.

Figure 4:
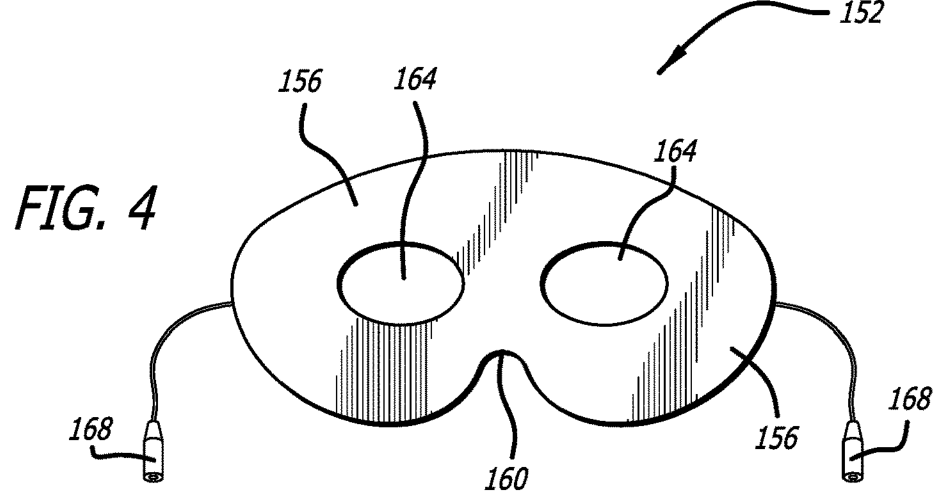
FIG. 4 illustrates a perspective view of an exemplary embodiment of an eye mask that may be coupled with the handheld electrostimulation skin treatment device of FIG. 1 in accordance with the present disclosure.

FIG. 4 illustrates a perspective view of an exemplary embodiment of an eye mask 152 in accordance with the present disclosure. The eye mask 152 is configured to be coupled with the treatment device 100 for the purpose of treating the skin and muscles surrounding the eyes. The eye mask 152 includes conductive strips 156 that are joined at a nose bridge 160. The conductive strips 156 may be applied around the eyes with the nose bridge 160 positioned above the user's nose. An eye opening 164 is disposed within each conductive strip 156 to allow the user receiving treatment to see. As will be appreciated, the eye mask 156 includes one or more electric connectors 168 that are configured to be plugged into the accessory connectors 128 of the treatment device 100 shown in FIG. 2. The electric connectors 168 and the accessory connectors 128 cooperate to pass electric microcurrent from the device 100 to the eye mask 152.

Figure 5:
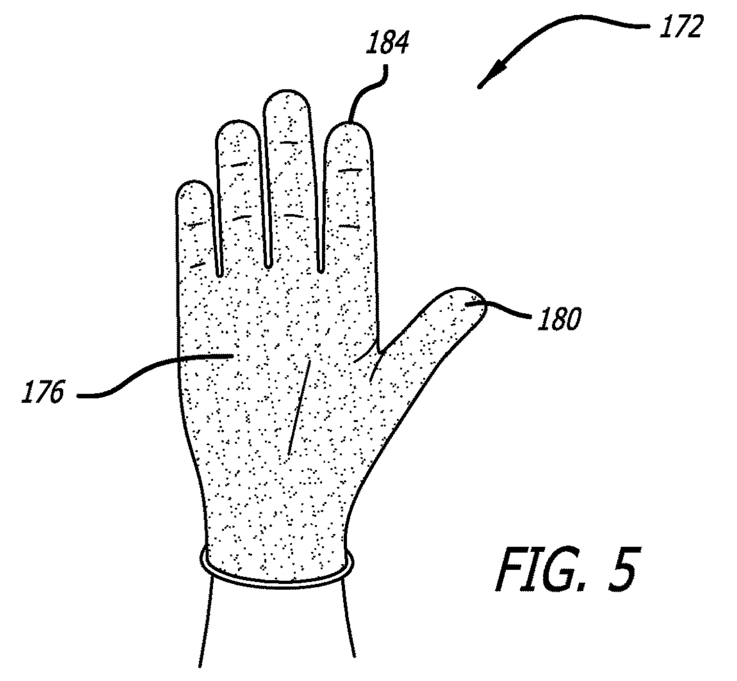
FIG. 5 illustrates an exemplary embodiment of a conductive glove that may be coupled with the handheld electrostimulation skin treatment device of FIG. 1 according to the present disclosure.

FIG. 5 illustrates an exemplary embodiment of a conductive glove 172 according to the present disclosure. In general, the conductive glove 172 may be coupled with the treatment device 100 by way of the accessory connectors 128, as described above. The conductive glove 172 is configured to facilitate a user manually manipulating the skin and muscles of the face while applying the electric microcurrent to the skin and muscles. As shown in FIG. 5, the conductive glove 172 may comprise an insulative material 176, including a thumb portion 180 and fingertip portions 184, that fits over the user's hand. In some embodiments, the thumb portion 180 may include a first electrode and at least one of the fingertip portions 184 may include a second electrode. Thus, a user may use a hand to manipulate the skin and muscles of the face while applying an electric microcurrent to the skin and muscles by way of the first and second electrodes comprising the conductive glove 172. Although not shown, the conductive glove 172 generally includes one or more electric connections that may be coupled with the accessory connectors 128 of the treatment device 100, whereby the electric microcurrent may be passed from the device 100 to the conductive glove 172.

Figures 6A, 6B:
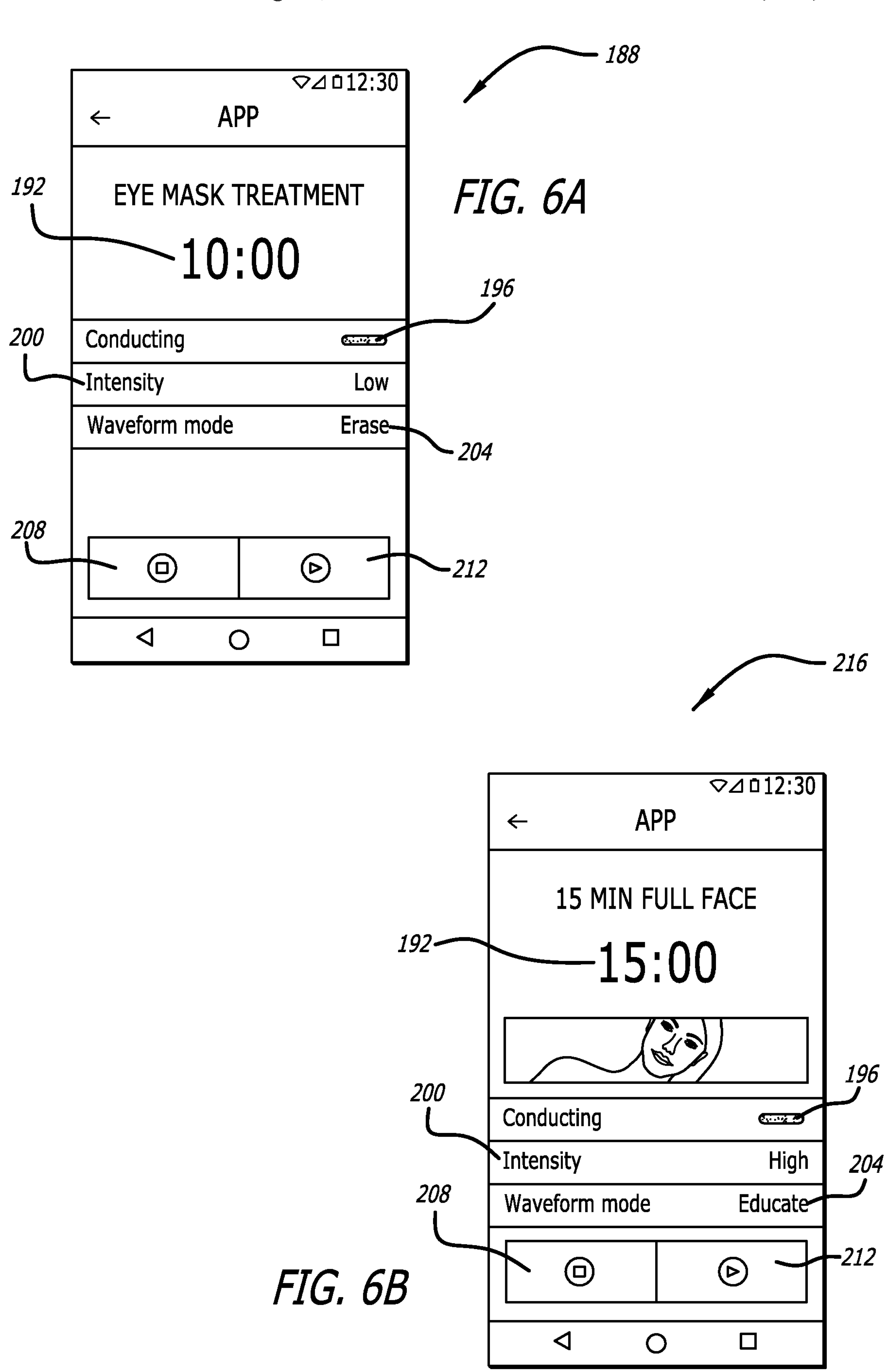
FIG. 6A illustrates an exemplary embodiment of an eye treatment screen that may be displayed on an external computing device that is coupled with the handheld electrostimulation skin treatment device of FIG. 1.
FIG. 6B illustrates an exemplary embodiment of a full-face treatment screen that may be displayed on an external computing device that is coupled with the handheld electrostimulation skin treatment device of FIG. 1.

As disclosed hereinabove with respect to FIG. 2, the treatment device 100 may include a USB connector 132 that may be coupled with an external computing device, such as a smartphone or tablet PC. It is contemplated that, in some embodiments, operation of the treatment device 100 may be controlled by way of a software application running on the external computing device. FIGS. 6A and 6B illustrate exemplary embodiments of treatment screens that may displayed to the user during operating the treatment device 100 by way of the software application.

FIG. 6A illustrates an exemplary embodiment of an eye treatment screen 188 that may be displayed on an external device that is coupled with the treatment device 100 by way of the USB connector 132. The eye treatment screen 188 may facilitate operation of the eye mask 152 when the eye mask 152 is coupled with the treatment device 100 by way of the accessory connectors 128, as described above. As shown in FIG. 6A, the eye treatment screen 188 includes a treatment timer 192, a conducting indicator 196, an intensity selector 200, and a waveform indicator 204. The treatment timer 192 displays the amount of time during which the treatment will be performed. In one embodiment, the eye mask treatment is performed for a set time of 10 minutes. The conducting indicator 196 displays the current state of the microcurrent being supply to the eye mask 152. The intensity selector 200 enables the user to control the intensity of the microcurrent being applied to the skin and muscles. In the illustrated embodiment of FIG. 6A, the intensity selector 200 is set to a "Low" setting. By contract, in the embodiment illustrated in FIG. 6B, the intensity selector 200 is set to a "High" setting.

The waveform indicator 204 displays how the electric microcurrent is being applied to the skin and muscles during treatment. In the illustrated embodiment of FIG. 6A, for example, the waveform indicator 204 displays Erase, indicating a program whereby the electric microcurrent is being applied in a manner intended to help erase fine lines in the user's skin. It is contemplated that the Erase program may be used in areas where it is desirable to lengthen the facial muscles or remove wrinkles. By contrast, in the embodiment illustrated in FIG. 6B, the waveform indicator 204 displays Educate, indicating a program whereby the electric microcurrent is being applied in a manner intended to re-educate the facial muscles. It is contemplated that the Educate program reaches deeper into facial muscles, thereby stimulating muscle re-education, toning and lifting effects.

As shown in FIG. 6A, the eye mask treatment screen 188 includes a Stop Treatment button 208 and a Start/Pause Treatment button 212. As will be appreciated, the button 212 enables the user to begin applying the electric microcurrent to treat the facial skin and muscles. It is contemplated that when the treatment begins, the treatment timer 192 begins counting down while the treatment is being applied to the user. The button 208 enables the user to cease applying the treatment, as desired. The treatment timer 192 may be reset to its initial setting when the button 208 is pressed. The button 212 may be used to temporarily pause the treatment without resetting the treatment timer 192. As such, pressing the button 212 while the treatment is paused causes the treatment timer 192 to continue counting down without being reset. Once the entire time period indicated by the treatment timer 192 has elapsed, the treatment ceases and the treatment timer 192 resets.

FIG. 6B illustrates an exemplary embodiment of a full-face treatment screen 216 that may be displayed on an external device that is coupled with the treatment device 100 by way of the USB connector 132. The full-face treatment screen 216 facilitates operation of the electrodes 124 of the treatment device 100 when manual manipulation of the facial skin and muscles is desired. The full-face treatment screen 216 is substantially similar to the eye mask treatment screen of FIG. 6A, with the exception that the full-face treatment screen 216 displays settings relating to treating the facial skin and muscles by way of the electrodes 124. For example, as shown in FIG. 6B, the treatment timer 192 indicates that the full-face treatment may be performed for a set time of 15 minutes. The conducting indicator 196 displays the current state of the microcurrent being supply to the electrodes 124. The intensity selector 200 is set to a "High" setting that is suitable for treatment by way of the electrodes 124. Further, the waveform indicator 204 displays Educate, indicating a program whereby the electric microcurrent reaches deeper into facial muscles, thereby stimulating muscle re-education, toning and lifting effects.

Similar to the eye mask treatment screen 188, described with respect to FIG. 6A, the full-face treatment screen 216 includes the Stop Treatment button 208 and the Start/Pause Treatment button 212. As described above, the button 212 enables the user to begin applying the electric microcurrent to treat the facial skin and muscles. The button 208 enables the user to cease applying the treatment and reset the treatment timer 192, as desired. The button 212 may be further used to temporarily pause the treatment without resetting the treatment timer 192. Thus, pressing the button 212 while the treatment is paused causes the treatment timer 192 to continue counting down without being reset. Once the entire time period indicated by the treatment timer 192 has elapsed, the treatment ceases and the treatment timer 192 resets.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A method for an electrostimulation treatment device, comprising:

disposing a handle section between a treatment end and an second treatment accessories end;

configuring the accessories end to couple with one or more external accessory devices including any of a lip mask, an eye mask, forehead mask, jawline mask or a conductive glove;

arranging one or more electrodes on the treatment end wherein the one or more electrodes disposed on opposite sides of the treatment end, wherein the electrodes are configured to supply electric current to skin and muscles of the user; and locating a power switch on the handle section along with a rechargeable battery and integrated circuitry.

2. The method of claim 1, wherein disposing the handle section includes adapting the handle section to be grasped in a hand of a practitioner.

3. The method of claim 2, wherein adapting the handle section includes configuring a curvature along the length of the handle section that orients the treatment end away from the hand of the practitioner.

4. The method of claim 1, wherein locating the power switch includes configuring the power switch to enable a practitioner to turn the treatment device on and off.

5. The method of claim 1, wherein disposing the handle section includes enclosing the rechargeable battery and circuitry within the handle section.

6. The method of claim 5, wherein enclosing the rechargeable battery and circuitry includes configuring the rechargeable battery and circuitry to apply microcurrent electricity to one or more of one or more electrodes and the accessories end when the power switch is turned on.

7. The method of claim 1, wherein arranging the one or more electrodes comprises configuring metallic spheres for manipulating the skin and muscles of a user to be treated.

8. The method of claim 1, wherein arranging the one or more electrodes includes configuring the one or more electrodes to supply electric current to the skin and muscles of the user.

9. The method of claim 1, wherein arranging the one or more electrodes includes configuring the one or more electrodes to be pressed against the skin so as to manipulate the skin and muscles such that the muscles are forced into a desired form for re-education.

10. The method of claim 1, wherein configuring the accessories end includes adapting the accessories end to couple with any of a lip mask, an eye mask, forehead mask, jawline mask, or a conductive glove.

11. The method of claim 1, wherein configuring the accessories end includes adapting the accessories end to receive a USB connector.

12. The method of claim 11, wherein adapting the accessories end includes configuring the USB connector to be coupled with an external computing device.

13. The method of claim 11, wherein adapting the accessories end includes configuring the USB connector to be coupled with the one or more external accessory devices.

14. The method of claim 13, wherein configuring the accessories end includes configuring the electrostimulation treatment device to be operated by way of a software application running on the external computing device.

15. The method of claim 2, wherein adapting the accessories end includes configuring accessory connectors to enable coupling the electrostimulation treatment device with the one or more external accessory devices.

16. The method of claim 15, wherein configuring the accessory connectors includes configuring any of a lip mask, an eye mask, forehead mask, jawline mask, or a conductive glove.

17. The method of claim 16, wherein configuring the lip mask comprises configuring the lip mask to be coupled with the electrostimulation treatment device for the purpose of treating the skin comprising and/or surrounding the lips.

18. The method of claim 16, wherein configuring the eye mask comprises configuring the eye mask to be coupled with the electrostimulation treatment device for the purpose of treating the skin and muscles surrounding the eyes.

19. The method of claim 16, wherein configuring the conductive glove comprises configuring the conductive glove to be coupled with the electrostimulation treatment device to facilitate manually manipulating the skin and muscles of the face while applying the electric microcurrent to the skin and muscles.

* * * * *